(12) United States Patent
Bogan, Jr. et al.

(10) Patent No.: US 8,198,477 B2
(45) Date of Patent: Jun. 12, 2012

(54) PROCESS FOR PRODUCTION OF ACROLEIN FROM GLYCEROL

(75) Inventors: Leonard Edward Bogan, Jr., Lansdale, PA (US); Mark Anthony Silvano, New Hope, PA (US)

(73) Assignee: Rohm and Haas Company

( * ) Notice: Subject to any disclaimer, the term of this patent is extended or adjusted under 35 U.S.C. 154(b) by 390 days.

(21) Appl. No.: 12/592,182

(22) Filed: Nov. 20, 2009

(65) Prior Publication Data
US 2010/0168472 A1 Jul. 1, 2010

Related U.S. Application Data

(60) Provisional application No. 61/203,554, filed on Dec. 24, 2008.

(51) Int. Cl.
  *C07C 51/16* (2006.01)
  *C07C 45/00* (2006.01)
(52) U.S. Cl. .................................... 562/532; 568/486
(58) Field of Classification Search .................. 562/532; 568/486
See application file for complete search history.

(56) References Cited

U.S. PATENT DOCUMENTS

| | | | |
|---|---|---|---|
| 1,916,743 | A | 7/1933 | Schwenk et al. |
| 2,042,224 | A | 5/1936 | Groli et al. |
| 2,558,520 | A | 6/1951 | Hoyt et al. |
| 4,246,374 | A | 1/1981 | Kopchik |
| 5,387,720 | A | 2/1995 | Neher et al. |
| 5,426,249 | A | 6/1995 | Haas et al. |
| 7,396,962 | B1 | 7/2008 | Dubois et al. |
| 7,655,818 | B2 | 2/2010 | Dubois et al. |
| 7,939,597 | B2 | 5/2011 | Bub et al. |
| 2007/0129570 | A1* | 6/2007 | Shima et al. ................. 562/538 |
| 2009/0068440 | A1 | 3/2009 | Bub et al. |
| 2009/0134357 | A1 | 5/2009 | Bub et al. |

FOREIGN PATENT DOCUMENTS

JP 2006290815 10/2006

OTHER PUBLICATIONS

Hawley, the Condensed Chemcial Dictionary, 1971, Van Nostrand Reinhold Co., 8th ed., p. 936, two pages.*
Leeds, A. R., "Acrolein-Urea", Journal of American Chemical Society, 1882, 4, p. 58-61.
Witzemann, Edgar J., "The Preparation of Acrolein", Journal of American Chemical Society, 1914, 36, p. 1766-1770.
Evans, William L., et al., "The Mechanism of Carbohydrate Oxidation, VI. The Action of Potassium Hydroxide on di-glycerc Aldehyde", Journal of American Chemical Society, 1926, 48, p. 2703-2714.
Adkins, Homer, et al., "Acrolein", Organic Syntheses, 1926, 6, p. 1-3.
Wohl, A., et al., "One the Preparation of Acrolein". Comm. from the Lab. of Org. Chem. of the Institute of Tech. 1912, 45, p. 2046-2054.

* cited by examiner

*Primary Examiner* — Taylor Victor Oh

(57) ABSTRACT

The present invention relates to a process for producing acrolein by liquid phase dehydration of glycerol by preparing a mixture of a catalyst suspended in an organic solvent comprising one or more vinyl polymers and glycerol; and then mixing and heating the mixture to between 150° C. and 350° C. to dehydrate the glycerol and form acrolein. The vinyl polymers are selected from the group consisting of polyolefins, polystyrene, and mixtures thereof. The polyolefins may be polyethylene, polypropylene, polybutylene, polyisobutylene, polyisoprene, polypentene, or mixtures thereof. The acrolein may be subjected to vapor phase oxidation in the presence of a catalyst, such as a mixed metal oxide, to produce acrylic acid.

9 Claims, No Drawings

PROCESS FOR PRODUCTION OF ACROLEIN FROM GLYCEROL

This invention claims priority to U.S. Provisional Application No. 61/203,554 filed Dec. 24, 2008.

FIELD OF THE INVENTION

The present invention relates to a process for the liquid phase dehydration of glycerol to produce acrolein and acrylic acid.

BACKGROUND OF THE INVENTION

Acrylic acid (AA) is currently made commercially by the two-step catalytic oxidation of propylene. More recent, but not-yet-commercial technology exists for its manufacture by the catalytic oxidation of propane. Propylene is a petroleum derivative, and its price reflects the growing scarcity and rising price of oil. Propane, derived from oil or natural gas liquids, makes a convenient fuel, and its price has risen as it has been used as a substitute for petroleum fuels in energy production. Both propylene and propane are non-renewable resources. It is desirable to find a renewable feedstock for the manufacture of acrylic acid.

A diesel fuel can be made from renewable materials by transesterification of natural fats and oils. Transesterification with methanol yields fatty acid methyl esters, also known as FAME or biodiesel, and glycerol. The amount of glycerol produced in this way has already outstripped demand, and the amount of this "waste" glycerol is projected to increase. It is desirable to find a use for this glycerol. Glycerol is also available as a by-product of hydrolysis of various oils and fats, as well as from waste fluids in soap production.

The dehydration of glycerol to acrolein, in either vapor or liquid phase, is well-known. A variety of acids have been used to catalyze this reaction, including mineral acids, potassium bisulfate, zeolites, Nafion composites, and modified zirconias. See, e.g., U.S. Pat. No. 2,042,224, U.S. Pat. No. 2,558,520, U.S. Pat. No. 5,387,720 and U.S. Patent Publication US2006/092272. In processes for liquid phase dehydration of glycerol, the catalyst can be suspended in an organic liquid, such as an alkane or a mixture of alkanes (e.g., hexadecane or paraffin wax). In such liquid phase processes, some of the solvent distills and is separated from the water into the acrolein product, necessitating separation and recycle of the solvent. Not only does this complicate the process and add cost to it, but since acrolein has some solubility in the solvent, some acrolein is lost in this process. Also, it is known that acrolein is highly reactive at elevated temperatures such as those used during dehydration of glycerol and, therefore, prolonged exposure to the heat of the reaction mixture will result in losses of the desired acrolein product. Thus, prompt removal of the acrolein product from the reaction mixture is important to maximize acrolein yields.

The vapor phase reaction is generally most selective when carried out in the presence of a large quantity of water, e.g., aqueous solutions containing 20% or less by weight glycerol. As the fraction of glycerol in the feed is increased, side reactions forming glycerol ether dimers and oligomers occur with greater frequency, lowering the overall acrolein yield. Dehydration of an aqueous solution of glycerol having a glycerol concentration of only 20% would require a relatively large reactor for a given productivity, increasing both capital and operating expenses. Additionally, it is mentioned in U.S. Pat. No. 5,387,720 that, while dehydration occurs using aqueous glycerol of greater than 40% by weight glycerol, the selectivity of the reaction to acrolein and the service life of the catalyst are appreciably reduced at higher concentrations, and a glycerol concentration of between 10 and 25% by weight glycerol is recommended.

International Patent Application Publication WO 2006/092272 describes the dehydration of 0.1-90% glycerol solution to acrolein followed by the vapor-phase oxidation of acrolein to AA. The dehydration is carried out using catalysts having a Hammett acidity $H_o$ of +2 to −3 for liquid-phase reactions, and −3 to −8.2 for gas-phase. While this patent application discusses liquid phase dehydration of glycerol to acrolein, no mention is made of an organic solvent.

U.S. Pat. No. 2,558,520 provides a process for liquid phase dehydration of glycerol to acrolein over a supported acidic or anhydrous phosphorous-based catalyst, using paraffin (alkane) hydrocarbons as a solvent. It is acknowledged that a small portion of the paraffin solvent distills over with the acrolein product.

Japanese Unexamined Patent Application Publication JP 2006-290815 describes the liquid phase dehydration of glycerol using a solid acid catalyst having a Hammett acidity $H_o$ between +3.3 and −5.6 in a solvent. This application provides working examples using potassium bisulfate as the catalyst, and solvents include alkanes and paraffin wax.

The present invention addresses the aforesaid problems by using a melt of one or more vinyl polymers of suitable molecular weight as the liquid solvent. The reaction proceeds as with alkane or paraffin wax, but without distillation of solvent with the acrolein product. Thus, the aforesaid problems with product separation, solvent recycle, and yield loss are obviated. Also, a more concentrated aqueous glycerol solution (i.e., greater than about 20% by weight glycerol) may be used as the feed to this process.

SUMMARY OF THE INVENTION

The present invention provides a process for producing acrolein by liquid phase dehydration of glycerol, comprising: a) preparing a mixture of: i) a catalyst suspended in an organic solvent comprising one or more vinyl polymers; and ii) glycerol; and then b) mixing and heating said mixture to between 110° C. and 350° C. to dehydrate the glycerol and form acrolein. The glycerol may comprise 40% to 100% by weight glycerol, with the balance being water, based upon the total weight of the glycerol. The one or more vinyl polymers are selected from the group consisting of polyolefins and polystyrenes.

This mixture may also include a polymerization inhibitor which may be selected from the group consisting of: benzoquinone ("BQ"), 4-hydroxy-TEMPO ("4HT"), phenothiazine ("PTZ"), hydroquinone ("HQ"), methyl hydroquinone ("MeHQ"), copper metal, and mixtures thereof.

The catalyst is selected from the group consisting of bisulfate salts, pyrosulfate salts, and mixtures thereof, for example, potassium bisulfate, potassium pyrosulfate, and mixtures thereof.

The one or more vinyl polymers has a viscosity of no greater than about 12 Pa*s at the reaction temperature and may be selected, for example, from the group consisting of: polyolefins, polystyrenes, and mixtures thereof. Suitable polyolefins may be for example, without limitation, polyethylene, polypropylene, polybutylene, polyisobutylene, polyisoprene, polypentene, etc.

The present invention also provides a process for producing acrylic acid from glycerol, comprising: a) liquid phase dehydration of glycerol to produce acrolein by the process according to claim 1; and b) vapor phase oxidation of said acrolein to produce acrylic acid. The of vapor phase oxidation of the acrolein may be performed in the presence of a mixed metal oxide catalyst.

DETAILED DESCRIPTION OF THE INVENTION

Generally, the present invention comprises dehydration of glycerol to acrolein and is performed in a liquid-phase process, using a salt of a sulfate, pyrosulfate, or bisulfate as catalyst suspended in an organic solvent comprising one or more vinyl polymers.

For example, bisulfate and pyrosulfate salts of Group 1A elements (e.g., lithium, sodium, potassium, etc.) are useful catalysts for this dehydration reaction. It has been found that potassium bisulfate, potassium pyrosulfate, and mixtures thereof, perform particularly well as the catalyst.

Useful vinyl polymers include polyolefins (such as polyethylene, polypropylene, polybutylene, polyisobutylene, polyisoprene, polypentene, etc.), polystyrenes, and mixtures thereof. Out of the polyolefins, polyethylene and polypropylene were found to be particularly suitable for use as the vinyl polymer solvent. The organic solvent may comprise a single type of vinyl polymer or a mixture of more than one type of vinyl polymer. Furthermore, the vinyl polymer, or mixture of vinyl polymers, should be less volatile than paraffin wax, for example having a boiling point, at atmospheric pressure, of greater than 400° C. However, a solvent that has a suitably low vapor pressure may be too viscous to perform well as a reaction medium for the liquid phase dehydration reaction of glycerol to acrolein. Thus, it is recommended, for example, that the viscosity of the vinyl polymer, or mixture of vinyl polymers, at reaction temperature, be up to about 12.0 Pascalseconds (Pa*s), for example, without limitation, up to about 5.0 Pa*s.

The glycerol may comprise between 10% and 100% glycerol by weight, with the balance being water, based on the total weight of the glycerol. For example, without limitation, the glycerol concentration may be between 20% and 100%, or between 40% and 100%, or between 50% and 100%, or even between 50% and 85%, by weight, based on the total weight of the glycerol solution.

The organic solvent is a liquid comprising a melt of one, or a mixture of more than one, type of vinyl polymer. The melt of one or more vinyl polymers is heated to typically a temperature somewhere between 100° C. and 150° C. to form a melt prior to addition of the glycerol. It is possible for the viscosity of the vinyl polymer melt to be too high, resulting in a reaction mixture that is too viscous to allow the dehydration reaction to proceed efficiently. It is known that polyolefins will degrade to polyolefins of lower molecular weight and lower viscosity when heated. Thus, in cases where one or more polyolefins are used, the polyolefin melt may be heated prior to addition of the glycerol thereto, to degrade the polyolefin(s) until the viscosity of the melt is reduced sufficiently to permit the dehydration reaction to proceed. The polyolefin can then be stabilized against degradation by addition of a radical inhibitor.

The concentration of catalyst used should be between 1% and 40% by weight, catalyst based on the polyolefin solvent, such as between 1% and 30% by weight, or between 5% and 20%, or between 6% and 20% by weight, or even between 10% and 15% by weight, based on the polyolefin solvent.

Acrolein is a very reactive molecule and, if not quickly chilled or converted to acrylic acid, it can readily react with alcohols to form aldols, or with itself to form vinyl or Diels-Alder addition products. If this addition reaction is permitted to go unchecked, an intractable, black solid (sometimes referred to as "disacryl") is formed. The only practical means to prevent this is to remove the acrolein product from heat or convert it, e.g., to acrylic acid, as quickly as possible. To facilitate distillation and removal of the acrolein product from the heated reaction mixture, the reaction vessel may be sparged with air or nitrogen. If other solvents, such as paraffin wax or lower alkanes, are used, it has been found that such sparging tends to cause more of the solvent to distill over with the acrolein product. Use of vinyl polymers as the solvent is beneficial in view of this issue since essentially none of the vinyl polymer solvent distills over with the acrolein product even when sparging is employed during the dehydration reaction.

The liquid phase dehydration of glycerol to acrylic acid may be performed in any vessel suitable for containing, heating and distilling the liquid reaction mixture comprising glycerol, catalyst and vinyl polymer solvent. For example, without limitation, a continuous stirred tank reactor (CSTR) or a wiped film evaporator (WFE, also known as a thin-film wiping still), or even an extruder, may be readily used to perform the aforedescribed dehydration and distillation a catalytic distillation type of vessel.

Where the liquid phase dehydration of glycerol is performed in accordance with the present invention in an extruder, a suitable extruder may have a generally cylindrical barrel with a feed port at one end, an extrusion outlet at an opposite end thereof, and an addition port and a vent port intermediate the inlet and extrusion outlet. The addition port is typically intermediate the inlet and the vent port, with the extrusion outlet farthest downstream of all. In practice, one or more vinyl polymers (solvent) and the selected catalyst are provided to the feed port and pass through the barrel of the extruder. The glycerol is introduced through the addition port and acrolein is removed through a vent port. Since the product Acrolein is volatile, removal via the vent port is practical and efficient. The extruded vinyl polymer leaving the extrusion port may be recycled to the feed port of the extruder.

Since the difference between the boiling points of glycerol (280° C.) and acrolein (53° C.) is so large, the liquid phase dehydration may be conducted at a relatively low temperature which allows continuous distillation of the acrolein product. For example, the glycerol, catalyst and vinyl polymer solvent are mixed and maintained at a reaction temperature between 150° C. and 350° C., such as between 200° C. and 300° C., or even between 220° C. and 280° C.

The liquid phase dehydration of glycerol to produce acrolein may also be performed under reduced pressure, such as at 700 mm Hg (0.92 atm), to facilitate distillation and removal of the acrolein and shift the reaction toward acrolein production.

Additionally, one or more polymerization inhibitors may be included in the glycerol-catalyst-solvent mixture to prevent polymerization of the acrolein product. Furthermore, it has been observed that the vinyl polymer solvent degrades at elevated temperatures such as those employed for this dehydration process. Thus, inhibitors may be useful to prevent or minimize losses of the vinyl polymers through degradation. Suitable polymerization inhibitors include one or more of the following: hydroquinone (HQ); 4-methoxyphenol (MEHQ); 4-ethoxyphenol; 4-propoxyphenol; 4-butoxyphenol; 4-heptoxyphenol; hydroquinone monobenzylether; 1,2-dihydroxybenzene; 2-methoxyphenol; 2,5-dichlorohydroquinone; 2,5-di-tert-butylhydroquinone; 2-acetylhydroquinone; hydroquinone monobenzoate; 1,4-dimercaptobenzene; 1,2-dimercaptobenzene; 2,3,5-trimethylhydroquinone; 4-aminophenol; 2-aminophenol; 2-N,N-dimethylaminophenol; 2-mercaptophenol;

4-mercaptophenol; catechol monobutylether; 4-ethylaminophenol; 2,3-dihydroxyacetophenone; pyrogallol-1,2-dimethylether; 2-methylthiophenol; t-butyl catechol; di-tert-butylnitroxide; di-tert-amylnitroxide; 2,2,6,6-tetramethyl-piperidinyloxy; 4-hydroxy-2,2,6,6-tetramethyl-piperidinyloxy; 4-oxo-2,2,6,6-tetramethyl-piperidinyloxy; 4-dimethylamino-2,2,6,6-tetramethyl-piperidinyloxy; 4-amino-2,2,6,6-tetramethyl-piperidinyloxy; 4-ethanoloxy-2,2,6,6-tetramethyl-piperidinyloxy; 2,2,5,5-tetramethyl-pyrrolidinyloxy; 3-amino-2,2,5,5-tetramethyl-pyrrolidinyloxy; 2,2,5,5-tetramethyl-1-oxa-3-azacyclopentyl-3-oxy; 2,2,5,5-tetramethyl-3-pyrrolinyl-1-oxy-3-carboxylic acid; 2,2,3,3,5,5,6,6-octamethyl-1,4-diazacyclohexyl-1,4-dioxy; salts of 4-nitrosophenolate; 2-nitrosophenol; 4-nitrosophenol; copper metal; copper dimethyldithiocarbamate; copper diethyldithiocarbamate; copper dibutyldithiocarbamate; copper salicylate; methylene blue; iron; phenothiazine (PTZ); 3-oxophenothiazine; 5-oxophenothiazine; phenothiazine dimer; 1,4-benzenediamine; N-(1,4-dimethylpentyl)-N'-phenyl-1,4-benzenediamine; N-(1,3-dimethylbutyl)-N'-phenyl-1,4-benzenediamine; N-nitrosophenyl hydroxylamine and salts thereof; nitric oxide; nitrosobenzene; benzoquinone; or isomers thereof. Particularly useful inhibitors are typical radical inhibitors including, but not limited to, benzoquinone ("BQ"), 4-hydroxy-TEMPO ("4HT"), phenothiazine ("PTZ"), hydroquinone ("HQ"), methyl hydroquinone ("MeHQ"), copper metal, and mixtures thereof. For example, the inhibitor may be added to the solvent-catalyst mixture prior to combining the glycerol with the solvent-catalyst mixture, or it may be added to the glycerol feed. Determination of the effective amount of inhibitor to be used will depend upon reaction conditions, as well as the quantity of glycerol and acrolein expected in the dehydration reaction mixture, and is well within the ability of persons of ordinary skill to calculate.

It has been found that when vinyl polymers, such as polyolefins or polystyrenes, are used as the solvent for the catalyst, very little of the vinyl polymer solvent distills out of the mixture with the acrolein product. In practice, essentially none of the vinyl polymer solvent has distilled into the acrolein product.

It has also been found that some, but not all, polysiloxanes are suitable for use as the organic solvent. Since polysiloxanes are not vinyl monomers, the parameters for selection of suitable polysiloxanes are different. While certain polysiloxanes performed well as the organic solvent, others were too viscous to permit the dehydration reaction to proceed.

The acrolein can be converted to acrylic acid by methods well-known in the art. For example, without limitation, catalytic vapor phase oxidation of acrolein may be performed in the presence of a mixed metal oxide, at temperatures between 180° C. and 420° C., such as between 200° C. and 390° C. Suitable mixed metal oxides are well-known to persons of ordinary skill in the art and include, but are not limited to, molybdenum-vanadium based compounds, palladium-phosphorus-antimony based compounds, and cobalt-iron-bismuth-tungsten-molybdenum-zinc based compounds.

For example, catalyst compositions according to the following empirical formula are known to catalyze the vapor phase conversion of acrolein to acrylic acid:

$$Mo_aV_bCu_c(W)_d(Sb)_e(A)_f(G)_g(Y)_hO_x;$$

wherein A is at least an element selected from among alkali metal elements, and thallium; G is at least one element selected from among alkalai earth metals and zinc; Y is at least one element selected among Nb, Mn, Fe, Co, Ge, Sn, As, Ce, Ti, and Sm; O is oxygen; and wherein a, b, c, d, e, f, g, h, and x are the relative atomic ratios of the respective elements Mo, V, Cu, W, Sb, A, G, Y and O, where a is 12, b is 0.5-12, c is less than or equal to 6, d is 0.2-10, e is positive and less than or equal to 10; f is 0-0.5; g is 0-1; h is positive and less than 6; and x is a positive numerical value determined by the oxidation state of the other elements.

Another suitable molybdenum-vanadium based mixed metal oxide suitable for oxidation of acrolein to acrylic acid is represented by the following empirical formula:

$$Mo_aV_bW_cCu_dX_eY_f$$

wherein X is at least one element selected from the group consisting of zirconium and titanium, Y is at least one element selected from the group consisting of magnesium, calcium, strontium, and barium, and the subscripts a, b, c, d, e, and f are such that, when a is 12, b=1 to 14, 0<c=12, 0<d=6, 0<e=10, and f=0 to 3; 2.0<(Cu+X)=10.0 and 0.25=(Cu/X)=6.0.

Still another suitable molybdenum-vanadium based mixed metal oxide suitable for oxidation of acrolein to acrylic acid is represented by the following empirical formula:

$$Mo_aV_bE_cX_dO_e,$$

wherein Mo is molybdenum, V is vanadium, E is at least one element selected from the group consisting of tellurium and antimony, and X is at least one element selected from the group consisting of niobium, tantalum, titanium, aluminum, zirconium, chromium, manganese, iron, Rh, nickel, platinum, bismuth, indium, As, Ge, tin, lithium, sodium, potassium, rubidium, magnesium, calcium, barium, silver, lead, and phosphorous; and when a=1, b=0.01 to 1.0, c=0.01 to 1.0, d=0.01 to 1.0, and e is dependent on the oxidation state of said other elements Additionally, catalyst compositions according to the following empirical formula are known to catalyze the vapor phase conversion of acrolein to acrylic acid:

$$Pd_aP_bSb_cO_d$$

wherein a, b, c and d are the relative atomic ratios of the respective elements Pd, P, Sb and O, wherein, when a is 1, b is 1 to 42, c is 0 to 15, and d is a number which is of itself determined by the total valences of the other elements.

It is noted that endpoints of ranges are considered to be definite and are recognized to incorporate within their tolerance other values within the knowledge of persons of ordinary skill in the art, including, but not limited to, those which are insignificantly different from the respective endpoint as related to this invention (in other words, endpoints are to be construed to incorporate values "about" or "close" or "near" to each respective endpoint). The range and ratio limits, recited herein, are combinable. For example, if ranges of 1-20 and 5-15 are recited for a particular parameter, it is understood that ranges of 1-5, 1-15, 5-20, or 15-20 are also contemplated and encompassed thereby.

The viscosity of the vinyl polymer melt is measured by a parallel plate method. More particularly, the viscosities reported in the following examples were measured on a TA Instruments ARES-LS rheometer using 50 mm diameter, parallel plate fixtures. The zero position of the plates was determined at the desired test temperature before sample loading and a sample gap of 0.5 mm was used for all testing. Samples were allowed to melt onto the lower plate before setting the gap to eliminate bubbles. The samples were tested in a Dynamic Frequency Sweep mode from 500 rad/s to 1 rad/s at six equally spaced increments per decade on a logarithmic scale. An applied strain of 10% was applied to the samples. The complex viscosity of the fluids was typically invariant at frequencies below 100 rad/s, therefore all of the complex viscosity values below 100 rad/s were averaged together to give the reported viscosity values.

Specific applications of the process of the present invention will now be described in the context of the following comparative and working examples, the parameters and results of which are listed in Table 1 below.

EXAMPLES

Comparative Example 1

In a four-neck, round-bottom flask equipped with stirrer, Dean-Stark trap with condenser, and above-surface feed inlet, heated 13.75 g high-density polyethylene (Aldrich, MFI 42 g/10 min at 190° C./2.16 kg) and 3.0 g potassium bisulfate to 240° C. at a controlled pressure of 700 mm Hg, with stirring. The mixture was too viscous for reliable stirring.

Comparative Example 2

In a four-neck, round-bottom flask equipped with stirrer, Dean-Stark trap with condenser, and above-surface feed inlet, heated 13.75 g polyethylene (Aldrich, weight average molecular weight, "$M_w$", 4000, number average molecular weight, "$M_n$", 1700, viscosity=0.15 Pa*s at 125° C.) and 3.0 g potassium bisulfate to 240° C. at a controlled pressure of 700 mm Hg, with stirring. At a rate of 8.0 ml/hr, added 33.53 g of a 50% by weight ("w/w") solution of glycerol in water to the flask. A significant amount of solvent distilled over in the condenser with the acrolein product.

Working Example 1

In a four-neck, round-bottom flask equipped with stirrer, Dean-Stark trap with condenser, air inlet (flow rate 19.8 standard cubic centimeters, "sccm"), and sub-surface feed inlet, heated 19.9 g linear low-density polyethylene (LLDPE, Aldrich, weight average molecular weight, "$M_w$", 35000, number average molecular weight, "$M_n$", 7700, viscosity=78 P at 150° C., MFI 2250 g/10 min at 190° C./2.16 kg) and 3.0 g potassium bisulfate to 240° C. at a controlled pressure of 700 mm Hg, with stirring. The side arm leading to the Dean-Stark trap was insulated. At a rate of 5.0 ml/hr, added 27.32 g of an 80% w/w solution of glycerol in water containing 1000 parts per million ("ppm") 4-hydroxy-2,2,6,6-tetramethylpiperidinyloxy ("4HT") and 1000 ppm benzoquinone (BQ) to the flask. No solids collected in the condenser or any of the traps. Glycerol conversion was 97.1%, acrolein yield was 73.2%, carbon accountability was 87.9%, and mass accountability was 99.8%.

Working Example 2

In a four-neck, round-bottom flask equipped with stirrer, Dean-Stark trap with condenser, air inlet (flow rate 23.3 sccm), and sub-surface feed inlet, heated 101.3 g linear low-density polyethylene (LLDPE, Aldrich, $M_w$ 15000, $M_n$ 5500, viscosity=37.2 P at 150° C.) and 15.4 g potassium bisulfate to 240° C. at a controlled pressure of 700 mm Hg, with stirring. The side arm leading to the Dean-Stark trap was insulated. At a rate of 25.7 ml/hr, added 128.05 g of an 80% w/w solution of glycerol in water containing 1000 ppm 4-hydroxy-TEMPO (4HT) and 1000 ppm benzoquinone (BQ) to the flask. No solids collected in the condenser or any of the traps. Glycerol conversion was 92.7%, acrolein yield was 71.1%, carbon accountability was 86.7%, and mass accountability was 99.5%.

Working Example 3

The same procedure was followed as in Working Example 2, except that the solvent was a polypropylene (PP, Aldrich, $M_w$ 19600, $M_n$ 5400, viscosity=23 P at 190° C.). Glycerol conversion was 63.5%, acrolein yield was 33.7%, carbon accountability was 74.8%, and mass accountability was 99.2%.

Working Example 4

The same procedure was followed as in Working Example 2, except that the solvent was a polypropylene (PP, Aldrich, $M_w$ 14000, $M_n$ 3700, viscosity=10 P at 190° C.). Glycerol conversion was 76.8%, acrolein yield was 43.4%, carbon accountability was 71.5%, and mass accountability was 98.9%.

Working Example 5

The same procedure was followed as in Working Example 2, except that the solvent was an isotactic polypropylene (PP, Aldrich, $M_w$ 12000, $M_n$ 5000, viscosity=6.0 P at 190° C.). Glycerol conversion was 90.6%, acrolein yield was 71.7%, carbon accountability was 88.5%, and mass accountability was 98.6%.

Comparative Example 3

The same procedure was followed as in Working Example 2, except that the solvent was a perfluoropolyether (Fomblin Y 06/6). Glycerol conversion was 95.7%, acrolein yield was 47.3%, carbon accountability was 58.7%, and mass accountability was 98.9%. Some solvent (or solvent decomposition product) distilled over with product.

Comparative Example 4

The same procedure was followed as in Comparative Example 2, except that the solvent was a paraffin wax (Aldrich, m.p. 73-80° C.), as described in JP 2006-290815A. Glycerol conversion was 99.4%, acrolein yield was only 32.1%, carbon accountability was 39.5%, and mass accountability was 82.2%. A large amount of solvent distilled with the products.

Working Example 6

The same procedure was followed as in Working Example 2, except that the solvent was a polypropylene (Metocene 650Y, LyondellBasell, MFI 1800 g/10 min @ 230° C./2.16 kg), the pressure was atmospheric, and the temperature was 265° C. Glycerol conversion was 97.5%, acrolein yield was 72.8%, carbon accountability was 89.8%, and mass accountability was 99.2%.

Working Example 7

The same procedure was followed as in Working Example 8, except that the solvent was a polypropylene (Metocene 650X, LyondellBasell, MFI 1200 g/10 min @ 230° C./2.16 kg). Glycerol conversion was 97.4%, acrolein yield was 68.9%, carbon accountability was 84.2%, and mass accountability was 98.4%.

Working Example 8

The same procedure was followed as in Working Example 8, except that the solvent was a polypropylene (PP3746G, Exxon-Mobil, MFI 1500 g/10 min @ 230° C./2.16 kg). Glycerol conversion was 98.1%, acrolein yield was 68.8%, carbon accountability was 73.7%, and mass accountability was 98.8%.

Working Example 9

The same procedure was followed as in Working Example 8, except that the solvent was a polypropylene (PP3546G, Exxon-Mobil, MFI 1200 g/10 min @ 230° C./2.16 kg). Glycerol conversion was 99.3%, acrolein yield was 68.7%, carbon accountability was 82.0%, and mass accountability was 99.3%.

Comparative Example 5

The same procedure was followed as in Working Example 2, except that the solvent was a polyethylene (LLDPE, DNDA1082, Dow Chemical, MFI 140 g/10 min @ 190° C./2.16 kg). The run could not be completed because the solvent was too thick.

Working Example 10

The same procedure was followed as in Working Example 2, except that the solvent was a polystyrene (Polysciences, catalogue. no. 23637, MW 800-5000). Glycerol conversion was 88.9%, acrolein yield was 69.0%, carbon accountability was 89.2%, and mass accountability was 97.7%.

Working Example 11

Reaction in Extruder

In a twin screw counter-rotating extruder (e.g. 0.8" Welding Engineers twin screw extruder, or Werner-Pfleiderer ZDS-L 28) set up with a feed port for introducing polymer in solid form such as granule, pellet, or powder, an addition port or ports for introducing glycerol or aqueous glycerol solution (10-99% w/w glycerol) at elevated pressure, an extruder barrel heated electrically or with oil in five (1-10) separate zones, a die which serves as the exit port for the polymer, and a vent port or ports operated at substantially atmospheric pressure or under vacuum and located in the last zone, a mixture of 15% w/w (0.1-50%) potassium bisulfate (or similar) catalyst, 1000 ppm benzoquinone (or other, suitable inhibitor), and Metocene 650Y polypropylene (or other appropriate polyolefin or polystyrene) is introduced via the feed port.

Glycerol or aqueous glycerol solution (10-99% w/w glycerol) is introduced into the extruder barrel via an addition port located just after (downstream of) a non-flighted screw section (compounder) which forms a vapor seal which keeps the glycerol reagent from going back toward the feed port. The unreacted reagent as well as the volatile products and by-products of the reactor are removed at the vent. The mixture of polymer and catalyst leaves the extruder through the outlet port, or die, in melt form, and can be recycled either in melt form or after cooling and granulating or palletizing, to the feed port. The following Table 2 provides suitable extrusion process parameters in accordance with the present invention.

TABLE 1

Summary of solvent characterization and performance

| Example | Polymer | visc./temp. | MFI (g/10 min) (190° C./2.16 kg) | MFI (g/10 min) (230° C./2.16 kg) | glycerol conversion (%) | acrolein yield (%) | parallel plate viscosity (Pa · s) | | |
|---|---|---|---|---|---|---|---|---|---|
| | | | | | | | 220° C. | 240° C. | 260° C. |
| Comp. 1 | polyethylene | | 42 | | too viscous | | 132.6 | 98.4 | 73.7 |
| Comp. 2 | polyethylene | 1.5 P/125° C. | | | distills | | | | |
| 1 | polyethylene | 78 P/150° C. | 2250 | | 97.1 | 73.2 | 1.67 | 1.23 | 0.88 |
| 2 | polyethylene | 37.2 P/150° C. | — | | 92.7 | 71.1 | 0.73 | 0.49 | 0.36 |
| 3 | polypropylene | 23 P/150° C. | | | 63.5 | 33.7 | 1.06 | 0.74 | 0.48 |
| 4 | polypropylene | 10 P/190° C. | | | 76.8 | 43.4 | 0.47 | 0.31 | 0.23 |
| 5 | polypropylene | 6.0 P/190° C. | | | 90.6 | 71.7 | 0.30 | 0.23 | 0.19 |
| 6 | polypropylene | | | 1800 | 97.5 | 72.8 | 3.91 | 2.57 | 1.29 |
| 7 | polypropylene | | | 1200 | 97.4 | 68.9 | 6.03 | 3.94 | 2.49 |
| 8 | polypropylene | | | 1500 | 98.1 | 68.8 | 7.97 | 4.90 | 4.04 |
| 9 | polypropylene | | | 1200 | 99.3 | 68.7 | 11.45 | 7.17 | 4.74 |
| 10 | polystyrene | | | | 88.9 | 69.0 | | | |
| Comp. 4 | perfluoropolyether | | | | 95.7 | 47.3 | | | |
| Comp. 5 | polyethylene | | 140 | | too viscous | | 27.62 | 19.37 | 14.25 |

TABLE 2

| Polymer feed rate (g/min) | glycerol concentration | glycerol feed rate (g/min) | extruder rpm | avg. barrel temp. (° C.) | glycerol conversion (%) | acrolein yield (%) |
|---|---|---|---|---|---|---|
| 50 | 80 | 1 | 300 | 260 | 90 | 80 |
| 10-100 | 10-100 | 0.05-50 | 100-500 | 200-350 | | |

We claim:

1. A process for producing acrolein by liquid phase dehydration of glycerol, comprising:
   a) preparing a mixture of:
      i) a catalyst suspended in an organic solvent comprising one or more vinyl polymers;
      wherein the catalyst is selected from the group consisting of bisulfate salts, pyrosulfate salts, and mixtures thereof, wherein the organic solvent has a boiling point of greater than 400° C. at atmospheric pressure, and wherein the organic solvent has a viscosity of no greater than 12.0 Pa*s, at reaction temperature, and
      ii) glycerol; and
   b) mixing and heating said mixture to between 150° C. and 350° C. to dehydrate the glycerol and form acrolein.

2. The process of claim 1, wherein the glycerol comprises from 0 to 60% water, based upon the total weight of the glycerol.

3. The process of claim 1, wherein the catalyst is selected from the group consisting of potassium bisulfate, potassium pyrosulfate, and mixtures thereof.

4. The process of claim 1, wherein each of the one or more vinyl polymers is selected from the group consisting of: polyethyelene, polypropylene, polybutylene, polyisobutylene, polyisoprene, polypentene, polystyrene, and mixtures thereof.

5. The process of claim 4, wherein each of the one or more vinyl polymers is selected from the group consisting of: polyethylene, polypropylene, polystyrene, and mixtures thereof.

6. The process of claim 1, wherein said mixture is heated to a temperature between 220° C. and 280° C.

7. The process of claim 1, wherein the step of preparing a mixture further comprises adding polymerization inhibitor to the catalyst and organic solvent, wherein said polymerization inhibitor comprises at least one compound selected from the group consisting of: benzoquinone ("BQ"), 4-hydroxy-TEMPO ("4HT"), phenothiazine ("PTZ"), hydroquinone ("HQ"), methyl hydroquinone ("MeHQ"), copper metal, and mixtures thereof.

8. A process for producing acrylic acid from glycerol, comprising:
   a) liquid phase dehydration of glycerol to produce acrolein by the process according to claim 1; and
   b) vapor phase oxidation of said acrolein to produce acrylic acid.

9. The process of claim 8, wherein step b), the of vapor phase oxidation of said acrolein to produce acrylic acid is performed in the presence of a mixed metal oxide catalyst.

* * * * *